United States Patent
Diao et al.

(10) Patent No.: US 8,561,280 B2
(45) Date of Patent: Oct. 22, 2013

(54) ASSEMBLING A MULTI-FIBER MULTI-SPOT LASER PROBE

(75) Inventors: Chenguang Diao, Ellicott, MD (US); Ronald T. Smith, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 210 days.

(21) Appl. No.: 13/277,391

(22) Filed: Oct. 20, 2011

(65) Prior Publication Data

US 2013/0097843 A1 Apr. 25, 2013

(51) Int. Cl.
*A61B 18/18* (2006.01)
*B23P 11/02* (2006.01)
*B23Q 3/00* (2006.01)

(52) U.S. Cl.
USPC .................................... 29/447; 29/464; 606/4

(58) Field of Classification Search
USPC .............. 29/447, 464, 527.1, 527.2; 351/221, 351/246; 601/2; 606/4
See application file for complete search history.

(56) References Cited

U.S. PATENT DOCUMENTS

| | | | |
|---|---|---|---|
| 6,096,028 A * | 8/2000 | Bahmanyar et al. | 606/4 |
| 8,409,180 B2 * | 4/2013 | Blumenkranz et al. | 606/4 |
| 2011/0038174 A1 | 2/2011 | Papac et al. | |
| 2011/0144627 A1 | 6/2011 | Smith | |
| 2012/0065543 A1 * | 3/2012 | Ireland | 600/567 |
| 2012/0150159 A1 * | 6/2012 | Kunath-Fandrei et al. | 606/4 |
| 2013/0019452 A1 * | 1/2013 | Wertman et al. | 29/447 |

* cited by examiner

*Primary Examiner* — Alexander P Taousakis
(74) *Attorney, Agent, or Firm* — Keiko Ichiye

(57) ABSTRACT

In certain embodiments, assembling a multi-fiber multi-spot laser system includes heating a ferrule until an interior diameter of an interior volume of the ferrule has expanded to greater than a predetermined diameter. End portions of a number of optical fibers are disposed within the interior volume. The ferrule is cooled to allow a cross-section of the fibers to conform to a fiber pattern having the predetermined diameter. At least a portion of the ferrule is disposed within a connector body to yield at least a portion of an optical fiber connector. In certain embodiments, the ferrule is rotated with respect to the connector body to align the fiber pattern with a laser spot pattern.

19 Claims, 5 Drawing Sheets

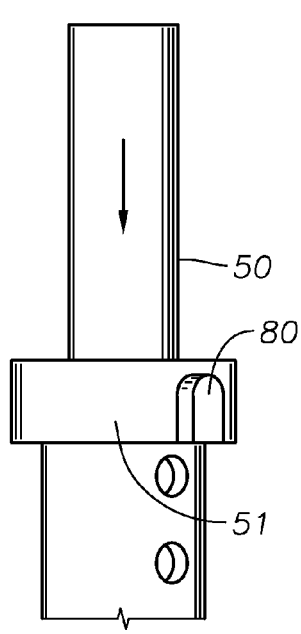
Fig. 5A
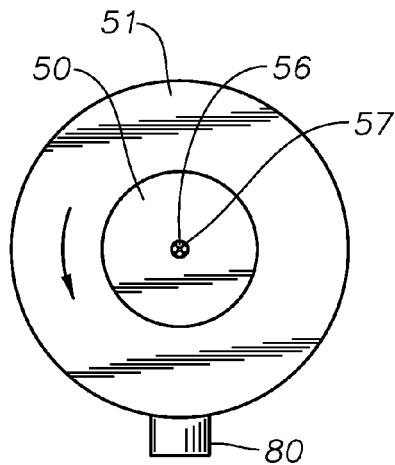
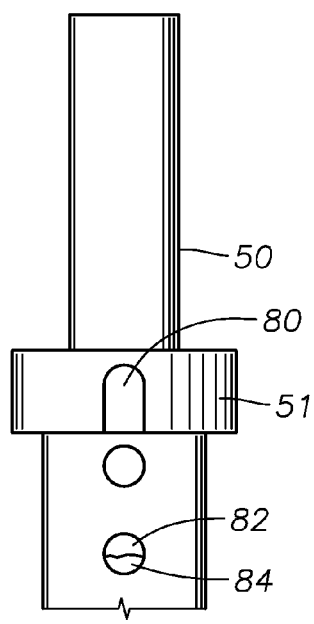
Fig. 5C
Fig. 5B
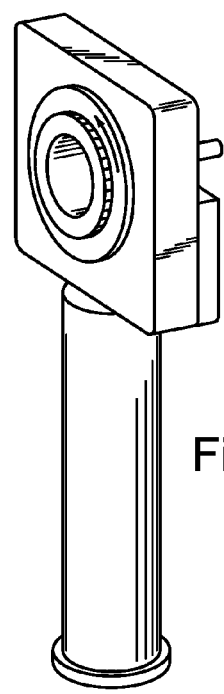
Fig. 6A
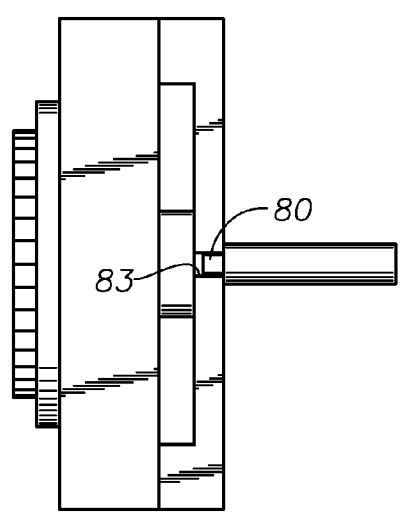
Fig. 6B

US 8,561,280 B2

ASSEMBLING A MULTI-FIBER MULTI-SPOT LASER PROBE

TECHNICAL FIELD

The present disclosure relates generally to laser systems, and more particularly to assembling a multi-fiber multi-spot laser probe.

BACKGROUND

Laser probes may be used for a variety of different purposes. In laser photocoagulation, a laser probe is used to cauterize blood vessels at laser burn spots across the retina. Certain types of laser probes burn multiple spots at a time, which may result in faster and more efficient photocoagulation. Some of these multi-spot laser probes split a single laser beam into multiple laser beams that exhibit a laser spot pattern and deliver the beams to an array of optical fibers that exhibit a corresponding fiber pattern. Typically, the fibers should be tightly packed so that the fiber pattern matches the laser spot pattern. Moreover, the laser spot pattern should be accurately aligned with the fiber pattern.

BRIEF SUMMARY

In certain embodiments, assembling a multi-fiber multi-spot laser system includes heating a ferrule until an interior diameter of an interior volume of the ferrule has expanded to greater than a predetermined diameter. End portions of a number of optical fibers are disposed within the interior volume. The ferrule is cooled to allow a cross-section of the fibers to conform to a fiber pattern having the predetermined diameter. At least a portion of the ferrule is disposed within a connector body to yield at least a portion of an optical fiber connector. In certain embodiments, the ferrule is rotated with respect to the connector body to align the fiber pattern with a laser spot pattern.

BRIEF DESCRIPTION OF THE DRAWINGS

Exemplary embodiments of the present disclosure will now be described by way of example in greater detail with reference to the attached figures, in which:

FIG. 5A through 5C illustrate aligning a fiber pattern with a key according to certain embodiments;

FIG. 6 illustrates a rotator for aligning a fiber pattern according to certain embodiments;

DETAILED DESCRIPTION OF THE INVENTION

Figure 1:
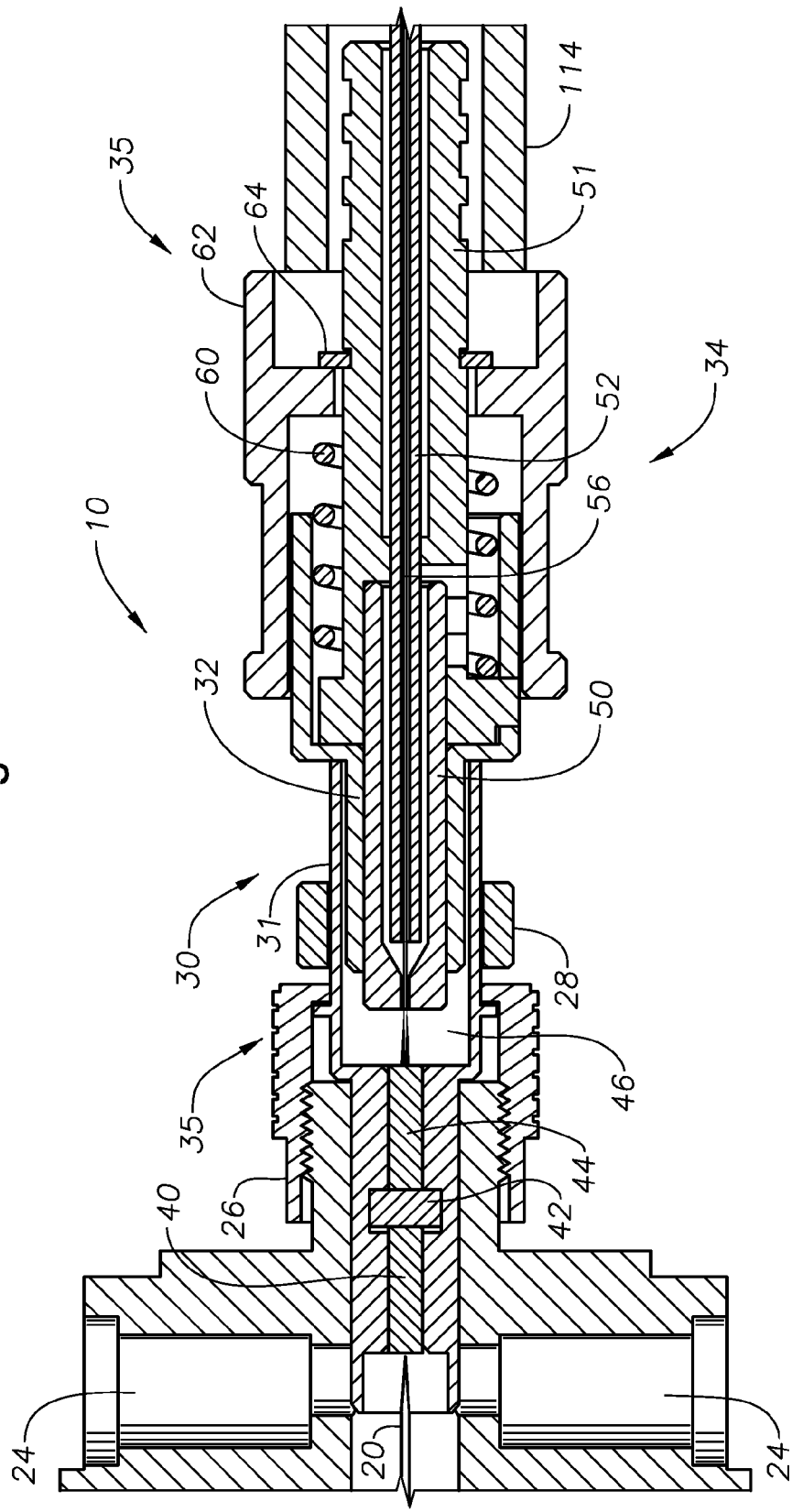
FIG. 1 illustrates an example of a multi-fiber multi-spot laser probe system that may be assembled according to certain embodiments.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

Figure 2:
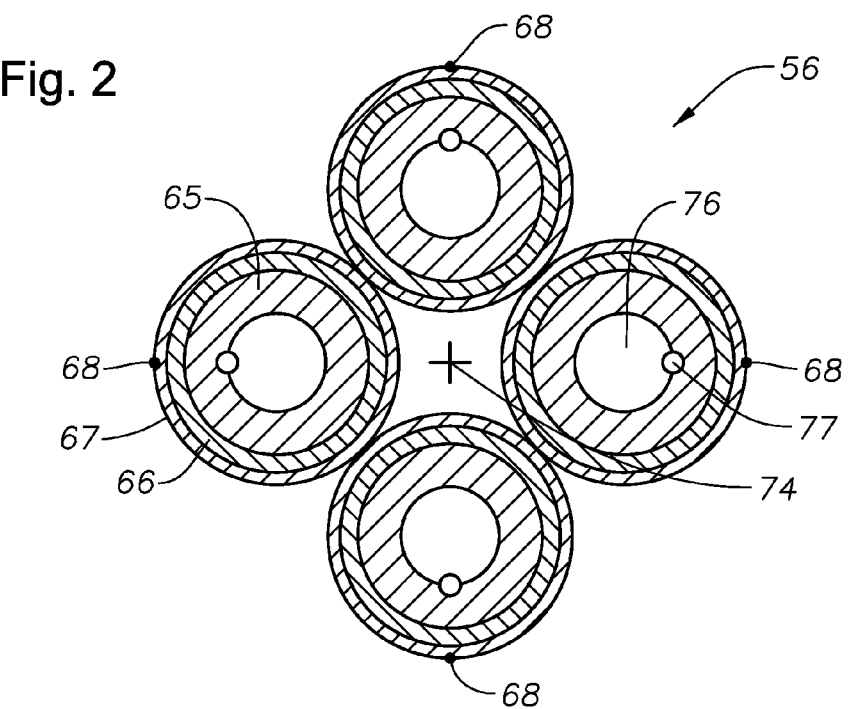
FIG. 2 illustrates an example of a laser spot pattern and a fiber pattern according to certain embodiments.

FIG. 1 through 3 illustrate an example of a multi-fiber multi-spot laser probe that may be assembled according to certain embodiments. In the illustrated example, system 10 includes a laser 20, laser port 24, an adapter 30, an optical fiber connector 34, a strain relief 114, and coupling devices 35 coupled as illustrated. Disposed within adapter 30 are a lens 40, a beam splitter 42, and a lens 44. Adapter 30, lens 44, and optical fiber connector 34 may form an air gap 46. Optical fiber connector 34 may include a ferrule 50 coupled to a connector body 51. A cylindrical insert 52 may be disposed within optical fiber connector 34, and a bundle of optical fibers 56 may be disposed within cylindrical insert 52. Coupling devices 35 include a threaded cylinder 26, a retaining ring 28, a spring 60, a coupling nut 62, and a C-clip 64.

In an example of operation, laser 20 may emit a laser beam that is focused towards lens 40, which collimates the laser beam. Beam splitter 42 splits the laser beam to yield a set of beams, or a multi-spot beam. Lens 44 refocuses the multi-spot beam onto optical fibers 56. Optical fibers 56 transmit the multi-spot beam through any suitable device, for example, a laser probe. The multi-spot beam may travel through a laser probe to any suitable target, such as the posterior region of an eye, such as a human eye. The multi-spot beam may be used for any suitable purpose, such as for performing photocoagulation on the retina of the eye.

In certain embodiments, laser 20 may be any suitable light source that can generate a laser beam. Laser port 24 may be any suitable structure that supports certain components of system 10 such that laser 20 can direct a laser beam towards lens 40. A lens 40 may be any suitable lens that can collimate a laser beam. For example, lens 40 may be a gradient index (GRIN) lens. Beam splitter 42 may be any suitable optical device that can split a laser beam to yield a multi-spot beam. For example, beam splitter 42 may be a diffraction beam splitter. Lens 44 may be any suitable lens that can refocus a multi-spot beam onto the focal plane defined by the proximal end faces of fibers 56. For example, lens 44 may be a GRIN lens.

Optical fiber connector 34 couples optical fibers 56 to adapter 30 to allow optical fibers 56 to receive the laser beam from adaptor 30. Optical fibers 56 may be arranged at an aperture of optical fiber connector 34 such that fibers 56 can receive a multi-spot beam.

FIG. 2 illustrates an example of a laser spot pattern of the multi-spot beam and a fiber pattern of optical fibers 56. A cross-section of any suitable number of optical fibers 56 may exhibit any suitable fiber pattern. The fiber pattern may be centered at a center point 74, and a cross section of a fiber 56 may be represented by a circle of the fiber pattern. In the illustrated example, the cross-section of four fibers 56 exhibits a fiber pattern of four circles. Each circle is equal distance from center point 74 and touches or approximately touches two other circles. A periphery point 68 of a circle is a point that is farthest from center point 74. The radius of the pattern is the distance between center point 74 and a periphery point 68. The pattern diameter is the two times the radius.

In another example (not illustrated), the cross-section of seven fibers 56 exhibits a fiber pattern of seven circles. A center circle is centered at center point 74. Each of six periphery circles is equal distance from center point 74 and touches or approximately touches the center circle and two other periphery circles. The radius of the pattern is the distance between center point 74 and a periphery point 68 of a periphery circle.

A cross-section of a multi-spot beam may yield any suitable laser spot pattern. In the illustrated example, four laser spots 76 yield a laser spot pattern with four spots. Each spot is equal distance from center point 74. An aiming beam spot 77 may be located within core 65 of fiber 56 to increase efficient optical coupling of aiming beam spot 77 into fiber 56. In the illustrated example, the laser spot pattern matches the fiber pattern such that each beam spot hits or substantially hits an optical fiber 56.

Figure 3B:
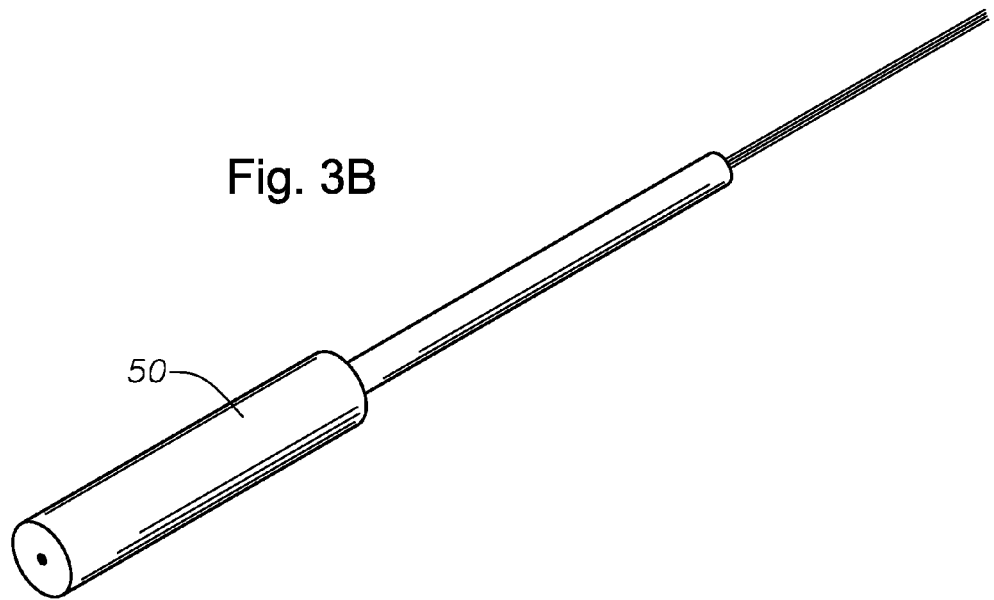
FIGS. 3A-3C illustrate an example of optical fibers disposed within a ferrule according to certain embodiments.
Figure 3A:
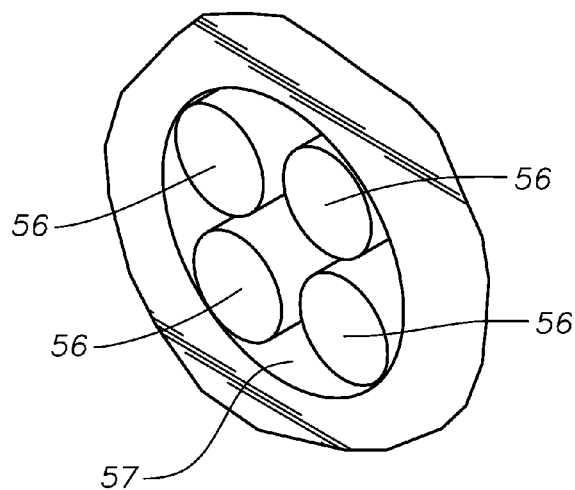
Figure 3C:
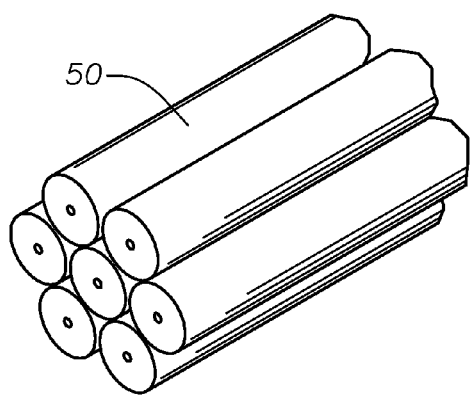

FIGS. 3A-3C illustrate an example of fibers 56 disposed within ferrule 50. Ferrule 50 holds optical fibers 56 in place to receive the multi-spot beam. Fibers 56 are configured to receive a multi-spot beam through an aperture 57 defined by a surface of ferrule 50.

Ferrule 50 may have any suitable shape, e.g., ferrule 50 may have a cylindrical shape with a surface that forms an interior volume that has an interior diameter. Ferrule 50 may have any suitable size, e.g., a length between 0.5 to 2.0 centimeters (cm) and an inner diameter between 200 to 300 micrometers (μm). In certain embodiments, the inner diameter may be selected to be approximately the same size as the fiber pattern diameter when cool and larger than (e.g., more than 0.5% larger than) the fiber pattern diameter when hot. Ferrule 50 may be made of any suitable material that expands while heating, for example, a metal such as stainless steel or aluminum alloy.

Referring back to FIG. 1, connector body 51 couples optical fiber connector 34 to adapter 30 and/or devices connected to a probe. Connector body 51 may have any suitable shape, e.g., a cylindrical shape within which optical fibers 56 may be disposed. Connector body 51 may have any suitable size, e.g., a length in the range of 1 to 3 centimeters (cm) and an outer diameter in the range of 0.5 to 1 cm.

An optical fiber 56 may be an optical waveguide that can transmit light. As seen in FIG. 2, an optical fiber 56 has a transparent core 65 surrounded by transparent cladding 66, which may in turn be surrounded by a jacket 67. Optical fiber 56 may comprise any suitable transparent material, e.g., glass. Optical fiber 56 may have any suitable size. For example, core 65 may have a diameter in the range of 50 to 100 μm, such as approximately 75 μm, and cladding 66 may have an outer diameter in the range of 80 to 150 μm, such as, 90 μm.

Returning to FIG. 1, coupling devices 35 couple together certain components of system 10. For example, threaded cylinder 26 and retaining ring 28 couple together adapter 30 and laser port 24. Spring 60, coupling nut 62, and C-clip 64 couple together optical fiber connector 34 and adaptor 30.

Figure 4:
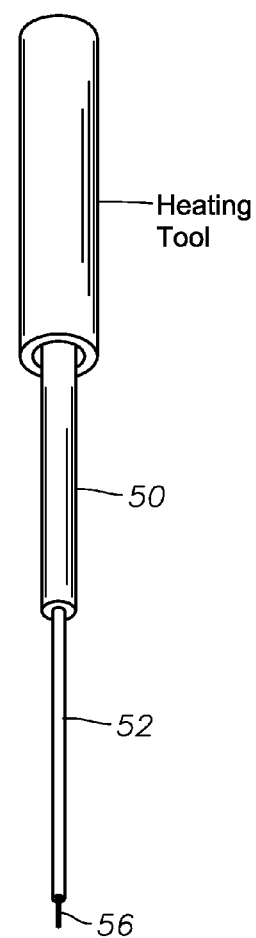
FIG. 4 illustrates heating a ferrule according to certain embodiments.

FIG. 4 through 8 illustrate an example of a method for assembling a multi-fiber multi-spot laser probe. FIG. 4 illustrates heating ferrule 50 until an interior diameter of an interior volume of ferrule 50 has expanded to greater than a predetermined diameter. In certain embodiments, the predetermined diameter may be the fiber pattern diameter. Ferrule 50 may be heated to any suitable temperature. In certain embodiments, the temperature may be determined using the coefficient of thermal expansion of the material of ferrule 50, which measures the fractional change in size per degree change in temperature at a constant pressure. In these embodiments, a temperature that yields a change in size such that the interior diameter is greater than the predetermined diameter may be selected. For example, a ferrule comprising stainless steel may be heated to a temperature greater than 450° Fahrenheit (F), such as 480° F.

When the interior diameter has expanded, the end portions of optical fibers 56 are disposed into the interior volume. Ferrule 50 is cooled to a temperature that allows the interior diameter to contract to the original size. For example, ferrule 50 may be cooled to room temperature. As the interior diameter contracts, the interior volume shrinks such that fibers 56 (within cylindrical insert 52) conform to the fiber pattern. If fibers 56 extend through aperture 57 to the exterior of ferrule 50, the fibers 56 may be cut at aperture 57.

In certain embodiments, an adhesive may be applied to bond the end portions of fibers 56 to ferrule 50. In certain embodiments, fibers 56 and ferrule 50 may be polished at the end that has aperture 57. Polishing papers of decreasing granularity may be used, e.g., 12 μm, 3 μm, and 0.3 μm.

FIG. 5A through 5C illustrate aligning the fiber pattern with key 80. FIG. 5A illustrates ferrule 50 disposed within connector body 51. Connector body 51 has a protrusion that forms a key 80. FIG. 5B illustrates a view of optical fiber connector 34 from a direction from which light is received at aperture 57. Ferrule 50 may be moved with respect to connector body 51 (which may mean moving body 51 with respect to ferrule 50 or vice-versa) in order to align the fiber pattern. Aligning the fiber pattern is described in more detail with reference to FIG. 6. FIG. 5C illustrates placing an adhesive 84 within an aperture 82 of connector body 51. Adhesive 84 may bond ferrule 50 and connector body 51 in order to prevent relative movement between ferrule 50 and body 51.

FIG. 6 illustrates a rotator 81 for aligning the fiber pattern. In the example, the fiber pattern may be aligned with respect to key 80 such that key 80 may be used to determine the alignment of the fiber pattern. Key 80 may be placed into a slot 83 of a rotator 81 to keep connector body 51 stationary. Ferrule 50 may be rotated until the fiber pattern is at the desired position with respect to key 80. The position of fiber pattern may be determined in any suitable manner. For example, a video camera system may detect the fiber pattern at aperture 57.

The desired alignment of the fiber pattern may be such that when optical fiber connector 34 is coupled to adapter 30, the fiber pattern matches the laser spot pattern. Key 80 indicates the alignment of the fiber pattern, so key 80 may be used to match the patterns.

Figure 7:
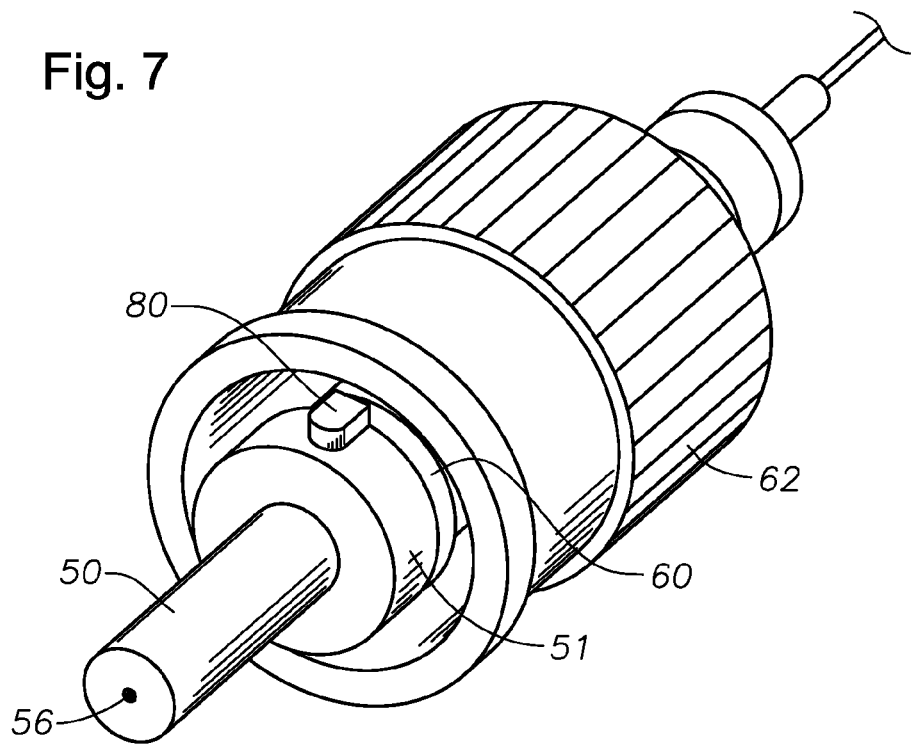
FIG. 7 illustrates an optical fiber connector with a spring and a threaded cylinder according to certain embodiments.

FIG. 7 illustrates fiber pattern aligned with key 80 in optical fiber connector 34 with spring 60 and coupling nut 62. Coupling nut 62 couples optical fiber connector 34 to adapter 30, and spring 60 secures the coupling of nut 62 and adapter 30. A C-clip 64 (shown in FIG. 1) may be used to secure coupling nut 62 to optical fiber connector 34

Figure 8:
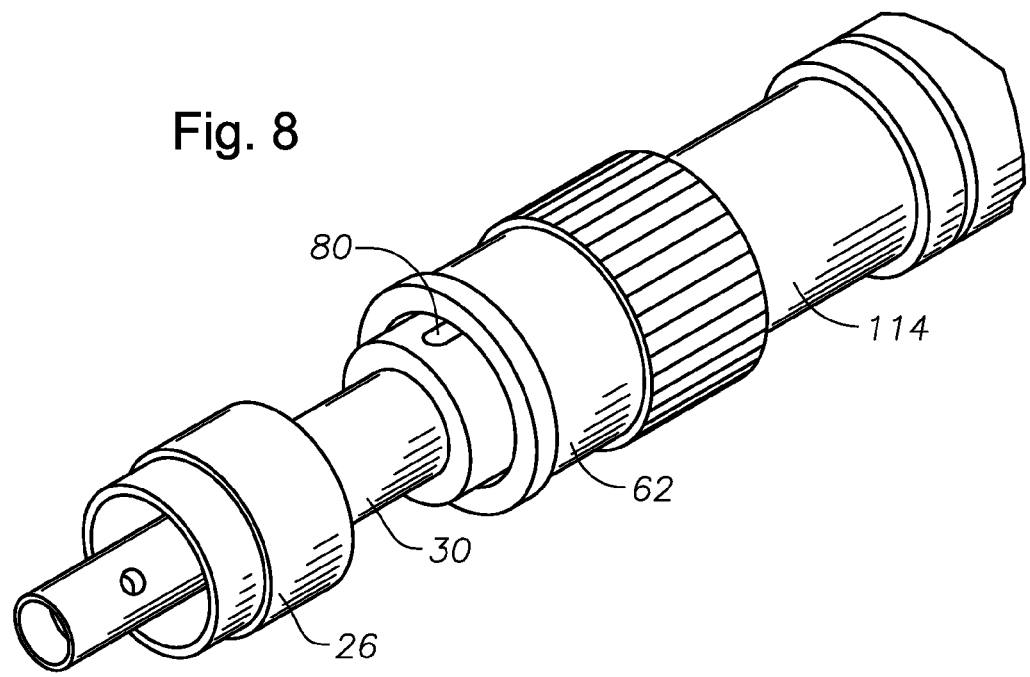
FIG. 8 illustrates an optical fiber connector with a threaded cylinder, an adapter, and a strain relief according to certain embodiments.

FIG. 8 illustrates optical fiber connector 34 with threaded cylinder 26, adapter 30, and a strain relief 114. Adapter 30 couples optical fiber connector 34 to laser port 24. Threaded cylinder 26 secures adapter 30 to laser port 24. Strain relief 114 alleviates strain on optical fiber connector 34. Strain relief 114 may comprise any suitable flexible material, for example, rubber.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A method comprising:
    heating a ferrule until an interior diameter of an interior volume of the ferrule has expanded to greater than a predetermined diameter, the ferrule having a cylindrical shape with a surface that defines the interior volume, the surface defining an aperture at an end of the cylindrical shape;
    disposing an end portion of each optical fiber of a plurality of optical fibers within the interior volume, the end portion disposed proximate to the aperture;
    cooling the ferrule to allow a cross-section of the fibers to conform to a fiber pattern having the predetermined diameter; and
    disposing at least a portion of the ferrule within a connector body to yield at least a portion of an optical fiber connecter.

2. The method of claim 1, the fiber pattern matching a laser spot pattern of a laser system, the optical fiber connecter configured to be coupled to the laser system.

3. The method of claim 1, further comprising:
    rotating the ferrule with respect to the connector body so the fiber pattern is at a desired alignment that corresponds to a laser spot pattern of a laser system.

4. The method of claim 1, further comprising:
    rotating the ferrule with respect to the connector body so the fiber pattern is at a desired alignment that corresponds to a laser spot pattern of a laser system; and
    bonding the ferrule and the connector body.

5. The method of claim 1, further comprising:
    rotating the ferrule with respect to the connector body so the fiber pattern is at a desired alignment with respect to a key of the connector body.

6. The method of claim 1, the heating further comprising heating the ferrule to a temperature greater than 450° Fahrenheit.

7. The method of claim 1, the cooling further comprising cooling the ferrule to room temperature.

8. The method of claim 1, further comprising:
    polishing the end portions of the optical fibers through the aperture.

9. The method of claim 1, further comprising:
    bonding the end portions of the optical fibers to the ferrule.

10. A method comprising:
    heating a ferrule until an interior diameter of an interior volume of the ferrule has expanded to greater than a predetermined diameter, the ferrule having a cylindrical shape with a surface that defines the interior volume, the surface defining an aperture at an end of the cylindrical shape;
    disposing an end portion of each optical fiber of a plurality of optical fibers within the interior volume, the end portion disposed proximate to the aperture;
    cooling the ferrule to allow a cross-section of the fibers to conform to a fiber pattern having the predetermined diameter, the fiber pattern matching a laser spot pattern of a laser system;
    disposing at least a portion of the ferrule within a connector body to yield at least a portion of an optical fiber connecter configured to be coupled to the laser system; and
    rotating the ferrule with respect to the connector body so the fiber pattern is at a desired alignment that corresponds to the laser spot pattern of a laser system.

11. The method of claim 10, further comprising:
    bonding the ferrule and the connector body.

12. The method of claim 10, the rotating further comprising:
    rotating the ferrule with respect to the connector body so the fiber pattern is at a desired alignment with respect to a key of the connector body.

13. The method of claim 10, the heating further comprising heating the ferrule to a temperature greater than 450° Fahrenheit.

14. The method of claim 10, the cooling further comprising cooling the ferrule to room temperature.

15. The method of claim 10, further comprising:
    polishing the end portions of the optical fibers through the aperture.

16. The method of claim 10, further comprising:
    bonding the end portions of the optical fibers to the ferrule.

17. A method comprising:
    heating a ferrule until an interior diameter of an interior volume of the ferrule has expanded to greater than a predetermined diameter, the ferrule having a cylindrical shape with a surface that defines the interior volume, the surface defining an aperture at an end of the cylindrical shape;

disposing an end portion of each optical fiber of a plurality of optical fibers within the interior volume, the end portion disposed proximate to the aperture;

cooling the ferrule to allow a cross-section of the fibers to conform to a fiber pattern having the predetermined diameter;

disposing at least a portion of the ferrule within a connector body to yield at least a portion of an optical fiber connecter; and coupling the optical fiber connecter to a cable configured to be coupled to a laser probe.

18. The method of claim 17, the fiber pattern matching a laser spot pattern of a laser system, the optical fiber connecter configured to be coupled to the laser system.

19. The method of claim 17, further comprising:

rotating the ferrule with respect to the connector body so the fiber pattern is at a desired alignment that corresponds to a laser spot pattern of a laser system.

* * * * *